US009453181B2

(12) United States Patent
Lupton

(10) Patent No.: US 9,453,181 B2
(45) Date of Patent: Sep. 27, 2016

(54) METHODS FOR REMOVING CONTAMINANTS FROM ALGAL OIL

(71) Applicant: Francis Stephen Lupton, Evanston, IL (US)

(72) Inventor: Francis Stephen Lupton, Evanston, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/561,702

(22) Filed: Dec. 5, 2014

(65) Prior Publication Data

US 2015/0094482 A1 Apr. 2, 2015

Related U.S. Application Data

(63) Continuation-in-part of application No. 13/326,057, filed on Dec. 14, 2011, now abandoned.

(51) Int. Cl.

*C07C 51/00* (2006.01)
*C11B 3/04* (2006.01)

(52) U.S. Cl.

CPC .................................... *C11B 3/04* (2013.01)

(58) Field of Classification Search

CPC ...................................................... C11B 3/04
See application file for complete search history.

(56) References Cited

U.S. PATENT DOCUMENTS

2012/0190872 A1* 7/2012 Cranford .................. C11B 1/02
554/207

OTHER PUBLICATIONS

Goel et al. (Flow Equalization and Neutralization, Handbook of Environmental Engineering, vol. 3: Physicochemical Treatment Process, pp. 21-45, 2005).*

* cited by examiner

*Primary Examiner* — Yevegeny Valenrod
*Assistant Examiner* — Blaine G Doletski

(57) ABSTRACT

Methods for removing contaminants from algal oil are provided. In an embodiment, a method comprises the steps of combining a sulfuric acid-aqueous solution that has a pH of about 1 or less with a contaminant-containing algal oil at treatment conditions effective to form an effluent. The effluent comprises a treated algal oil phase and contaminants in an acidic aqueous phase. The contaminants comprise metals, phosphorus, or combinations thereof. The acidic aqueous phase is removed from the effluent to form a contaminant-depleted algal oil.

18 Claims, 1 Drawing Sheet

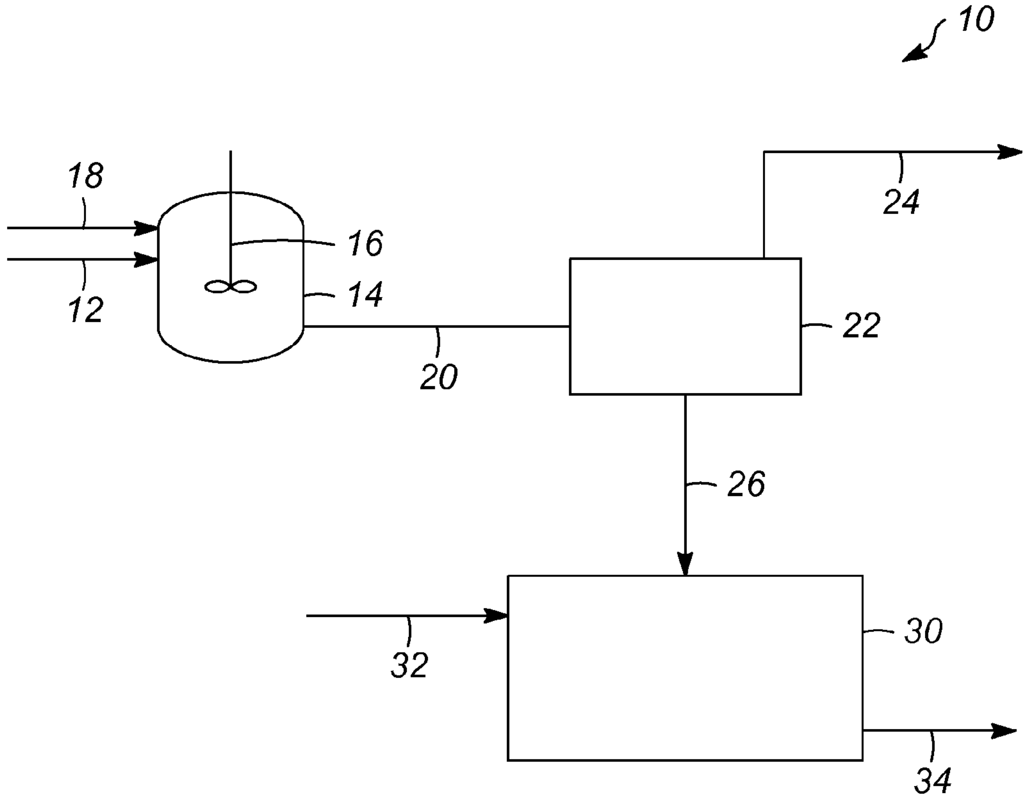
10
18
12
16
14
20
22
24
26
30
32
34

METHODS FOR REMOVING CONTAMINANTS FROM ALGAL OIL

CROSS-REFERENCE TO RELATED APPLICATION

This application is a Continuation-in-Part of copending application Ser. No. 13/326,057 filed Dec. 14, 2011, the contents of which are hereby incorporated by reference in its entirety.

STATEMENT REGARDING FEDERALLY SPONSORED RESEARCH OR DEVELOPMENT

This invention was made with Government support under DE-EE0003046 awarded by the U.S. Department of Energy. The Government has certain rights in this invention.

TECHNICAL FIELD

The present invention relates generally to methods for treating biomass-derived oils, and more particularly relates to methods for removing contaminants from algal oil to form a contaminant-depleted algal oil that can be further processed, for example, to produce a biofuel.

BACKGROUND

Algae are a diverse group of photosynthetic organisms that form a type of biomass that has attracted significant attention in recent years because of its ability to produce oil (hereinafter "algal oil"). Algal oil is rich in lipids and can be processed, e.g., via hydroprocessing and/or isomerization, to produce biofuels, such as bio-diesel, bio-jet, and the like.

Many of the extraction methods employed to extract oil from non-algae biomass feedstocks, such as vegetables, seeds, and the like, are non-disruptive type methods. These non-disruptive type methods generally do not disrupt the biomass cells and tend to produce relatively clean oils, e.g., vegetable oils, canola oil, sunflower oil, etc., with a substantial portion of the contaminants remaining behind in the biomass cells after the oil has been removed. Unfortunately, these non-disruptive type methods do not work well with algae because algae cells are relatively small, e.g., about 2 to about 20 nm, and have thick cell walls that make the extraction of algal oil more difficult.

Rather, algal oils are typically extracted from algae using disruptive type methods. Disruptive type methods include mechanical, thermal, enzymatic, or chemical methods that disrupt the algae cells to extract the algal oil as either a predominately lipid or esterified lipid oil or as liquefied algal biomass. However, by disrupting the algae cells, contaminants are readily removed from the algae cells together with the algal oil during extraction. These contaminants may include metals and phosphorus that are very problematic for downstream processing, such as processes for converting the algal oil to a biofuel. In particular, the metals and phosphorus contained in the algal oil are poisonous to many catalysts (e.g. hydroprocessing catalyst, isomerization catalyst, etc.) that are used to convert algal oils to biofuels. Unfortunately, current methods for removing contaminants from the algal oil prior to downstream oil conversion have proven to be unsatisfactory and currently limit the utilization of algal oils to produce biofuels.

Accordingly, it is desirable to provide methods for removing contaminants from algal oil to form a contaminant-depleted algal oil that may be further processed, for example, to produce a biofuel. Furthermore, other desirable features and characteristics of the present invention will become apparent from the subsequent detailed description and the appended claims, taken in conjunction with the accompanying drawings and this background.

BRIEF SUMMARY

Methods for removing contaminants from algal oil are provided herein. In accordance with an exemplary embodiment, a method for removing contaminants from algal oil comprises the steps of combining a sulfuric acid-aqueous solution that has a pH of about 1 or less with a contaminant-containing algal oil at treatment conditions effective to form an effluent. The effluent comprises a treated algal oil phase and contaminants in an acidic aqueous phase. The contaminants comprise metals, phosphorus, or combinations thereof. The acidic aqueous phase is removed from the effluent to form a contaminant-depleted algal oil.

In accordance with another exemplary embodiment, a method for removing contaminants from algal oil is provided. The method comprises the steps of introducing a contaminant-containing algal oil and a sulfuric acid-aqueous solution that has a pH of about 1 or less to a reactor. The reactor is operating at treatment conditions effective to form an effluent. The effluent comprises a treated algal oil phase and contaminants in an acidic aqueous phase. The contaminants comprise metals, phosphorus, or combinations thereof. The effluent is introduced to an oil-water separation zone to remove the acidic aqueous phase from the effluent and form a contaminant-depleted algal oil.

In accordance with another exemplary embodiment, a method for removing contaminants from algal oil is provided. The method comprises the steps of introducing a contaminant-containing algal oil and a sulfuric acid-aqueous solution at a predetermined acid to oil ratio of from about 1:4 to about 4:1 to a reactor. The reactor is operating at treatment conditions effective to form an effluent. The effluent comprises a treated algal oil phase and contaminants in an acidic aqueous phase. The contaminants comprise metals, phosphorus, or combinations thereof. The sulfuric acid-aqueous solution comprises sulfuric acid that is present in an amount of from about 1 to about 50 wt. % of the sulfuric acid-aqueous solution. The predetermined acid to oil ratio is defined by a first weight of the sulfuric acid-aqueous solution to a second weight of the contaminant-containing algal oil. The effluent is introduced to an oil-water separation zone to remove the acidic aqueous phase from the effluent and form a contaminant-depleted algal oil.

BRIEF DESCRIPTION OF THE DRAWINGS

The present invention will hereinafter be described in conjunction with the following drawing figures, wherein like numerals denote like elements, and wherein:

FIG. 1 is a block diagram of an apparatus for removing contaminants from algal oil in accordance with an exemplary embodiment.

DETAILED DESCRIPTION

The following Detailed Description is merely exemplary in nature and is not intended to limit the invention or the application and uses of the invention. Furthermore, there is no intention to be bound by any theory presented in the preceding background or the following detailed description.

Various embodiments contemplated herein relate to methods for removing contaminants from algal oil. Unlike the prior art, the exemplary embodiments taught herein combine a sulfuric acid-aqueous solution with a contaminant-containing algal oil at treatment conditions effective to form an effluent. The contaminants comprise metals and/or phosphorus, such as Ca, Fe, Mg, Na, Zn, K, and/or P. The sulfuric acid-aqueous solution is a concentrated acidic solution having a pH of about 1 or less. The inventor has found that the relatively low pH sulfuric acid-aqueous solution effectively digests the contaminants in the algal oil at the treatment conditions to form the effluent that comprises a treated algal oil phase and the contaminants digested in an acidic aqueous phase. The aqueous phase including the contaminants is removed from the effluent to form a contaminant-depleted algal oil. In an exemplary embodiment, the contaminant-depleted algal oil contains about 10 weight percent (wt. %) or less of the contaminants that were originally present in the contaminant-containing algal oil. As such, the contaminant-depleted algal oil may be passed along for further processing, for example, to produce a biofuel.

Referring to FIG. 1, a schematic depiction of an apparatus 10 for removing contaminants from algal oil in accordance with an exemplary embodiment is provided. As illustrated, a contaminant-containing algal oil stream 12 is introduced to a reactor 14. The contaminant-containing algal oil stream 12 comprises algal oil and contaminants. In an exemplary embodiment, the contaminant-containing algal oil stream 12 is a stream containing crude algal oil (e.g. “as extracted” algal oil). The crude algal oil may be obtained via a mechanical, thermal, enzymatic, or chemical disruptive method that disrupts the algae cells to extract the algal oil as is well known or by any other method known to those skilled in the art. Crude algal oil is also commercially available, for example, from Solix BioSystems, Inc., which is headquartered in Fort Collins, Colo.

In an exemplary embodiment, the contaminants in the contaminant-containing algal oil stream 12 comprise phosphorus and/or metals, such as Ca, Fe, Mg, Na, Zn, and/or K. The contaminants may also comprise other metals, such as Al, Co, Cr, Cu, Mn, Mo, Pb, Sn, Sr, Ti, and/or V. In an exemplary embodiment, the contaminant-containing algal oil stream 12 contains up to about 8,000 ppm or greater of total contaminants.

The reactor 14 may be a batch reactor or a continuous flow reactor. In an exemplary embodiment, the reactor 14 is a continuous stirred tank reactor (CSTR) that includes a mechanical mixing device 16. Alternatively, the reactor 14 may be any other type of reactor known to those skilled in the art for removing contaminants from oil to produce treated oil.

A sulfuric acid-aqueous solution stream 18 is introduced to the reactor 14. The sulfuric acid-aqueous solution stream 18 comprises sulfuric acid and water. In an exemplary embodiment, the sulfuric acid-aqueous solution stream 18 comprises sulfuric acid that is present in an amount of from about 1 to about 50 wt. %, for example from about 2 to about 50 wt. %, for example from about 5 to about 15 wt. %, such as about 10 wt. % of the sulfuric acid-aqueous solution stream 18. In an exemplary embodiment, the sulfuric acid-aqueous solution stream 18 has a pH of about 1 or less, for example from about 1 to about −1, for example from about 0 to about −0.5, such as about −0.1.

The sulfuric acid-aqueous solution stream 18 and the contaminant-containing algal oil stream 12 are introduced to the reactor at a predetermined acid to oil ratio. The predetermined acid to oil ratio is defined by a mass flow rate of the sulfuric acid-aqueous solution stream 18 to a mass flow rate of the contaminant-containing algal oil stream 12 (e.g. effectively a weight of the sulfuric acid-aqueous solution added to the reactor 14 to a weight of the contaminant-containing algal oil added to the reactor 14). In an exemplary embodiment, the predetermined acid to oil ratio is from about 1:4 to about 4:1, for example from about 1:2 to about 2:1, such as about 1:1.

As illustrated, the sulfuric acid-aqueous solution stream 18 and the contaminant-containing algal oil stream 12 are combined in the reactor 14 and agitated with the mechanical mixing device 16. The reactor 14 is operating at treatment conditions effective for the sulfuric acid-aqueous solution to digest the contaminants in the contaminant-containing algal oil to form an effluent 20. The effluent 20 comprises a treated algal oil phase and an acidic aqueous phase. The treated algal oil phase is substantially depleted of the contaminants that are now digested and substantially present in the acidic aqueous phase. In an exemplary embodiment, the treatment conditions include a temperature of from about 4 to about 25° C., a pressure of from about 80 to about 120 kPa, and a residence time of from about 30 minutes to about 8 hours, for example from about 1 to about 5 hours, such as from about 1 to about 2 hours. In another embodiment the temperature may range from about 4 to about 20° C. In another embodiment the temperature may range from about 4 to about 15° C. The residence time is defined by an amount of time that the contaminant-containing algal oil and the sulfuric acid-aqueous solution are in contact with each other in the reactor 14 to form the effluent 20. An advantage of the process is that the treatment may be conducted at ambient temperature, without any heat being added. The actual temperature of ambient temperature may vary across environments, and thus may cover a range of temperatures from about 4° C. to about 25° C., and over this temperature range the process has been found to be successful in the absence of external heat being applied.

The effluent 20 is introduced to an oil-water separation zone 22. The oil-water separation zone 22 removes the acidic aqueous phase including the contaminants from the effluent 20 using one or more separation vessels, fractionation columns, heaters, condensers exchangers, pipes, pumps, compressors, controllers, and/or the like. In an exemplary embodiment, the oil-water separation zone 22 comprises an American Petroleum Institute (API) oil-water separator that separates the effluent 20 based on the specific gravity difference between the treated algal oil phase and the acidic aqueous phase. As illustrated, the oil-water separation zone 22 separates the effluent 20 to form a contaminant-depleted algal oil stream 24 and an acidic contaminant-containing aqueous solution stream 26.

In an exemplary embodiment, the contaminant-depleted algal oil stream 24 contains about 10 wt. % or less, for example about 6 wt. % or less, for example about 4 wt. % or less, for example about 2 wt. % or less, such as from about 1 to about 0 wt. % of the contaminants that were originally present in the contaminant-containing algal oil stream 12. That is, for example, the contaminant-depleted algal oil stream 24 is algal oil that has been treated such that about 90 wt. % or greater, for example about 94 wt. % or greater, for example about 96 wt. % or greater, for example about 98 wt. % or greater, such as about 99 to about 100 wt. % of the contaminants originally present in the crude algal oil have been removed. The contaminant-depleted algal oil stream 24 is removed from the oil-water separation zone 22 and is passed along, for example, for further processing to produce a biofuel.

The acidic contaminant-containing aqueous solution stream 26 is removed from the oil-water separation zone 22 and is passed along and introduced to neutralizing zone 30. A base-containing composition 32 is introduced to the neutralizing zone 30. In an exemplary embodiment, the base-containing composition 32 is a solution having a pH of about 10 or greater, such as about 10 to about 14. In one example, the base-containing composition 32 is a sodium hydroxide aqueous solution that has a pH of about 10 to about 12. The base-containing composition contacts and neutralizes the acidic contaminant-containing aqueous solution stream 26 to form a salty contaminant-containing aqueous solution stream 34. The salty contaminant-containing aqueous solution stream 34 is removed from the neutralizing zone 30 for disposal.

Accordingly, methods for removing contaminants from algal oil have been described. Unlike the prior art, the exemplary embodiments taught herein combined a sulfuric acid-aqueous solution with a contaminant-containing algal oil at treatment conditions effective to form an effluent. The contaminants comprise metals and/or phosphorus, and the sulfuric acid-aqueous solution is a concentrated acidic solution having a pH of about 1 or less. The relatively low pH sulfuric acid-aqueous solution effectively digests the contaminants in the algal oil at the treatment conditions to form the effluent that comprises a treated algal oil phase and the contaminants digested in an acidic aqueous phase. The aqueous phase including the contaminants is removed from the effluent to form a contaminant-depleted algal oil. In an exemplary embodiment, the contaminant-depleted algal oil contains about 10 weight percent (wt. %) or less of the contaminants that were originally present in the contaminant-containing algal oil. As such, the contaminant-depleted algal oil may be passed along for further processing, for example, to produce a biofuel.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method for removing contaminants from algal oil, the method comprising the steps of:

extracting a contaminant-containing algal oil from algae cells to form a crude algal oil that comprises the contaminant-containing algal oil and that is substantially free of the algae cells;

combining a sulfuric acid-aqueous solution that has a pH of about 1 or less with the crude algal oil at treatment conditions that include a temperature of from about 4 to about 25° C. and at a predetermined acid to oil ratio of from about 1:4 to about 4:1, wherein the predetermined acid to oil ratio is defined by a first weight of the sulfuric acid-aqueous solution to a second weight of the contaminant-containing algal oil to form an effluent that comprises a treated algal oil phase and contaminants in an acidic aqueous phase, wherein the contaminants comprise metals, phosphorus, or combinations thereof;

removing the acidic aqueous phase from the effluent to form a contaminant-depleted algal oil containing about 10 wt. % or less of the contaminants that were originally present in the contaminant-containing algal oil.

2. The method of claim 1, wherein the step of combining comprises combining the sulfuric acid-aqueous solution that has the pH of from about 1 to about −1 with the contaminant-containing algal oil.

3. The method of claim 1, wherein the step of combining comprises combining the sulfuric acid-aqueous solution that has the pH of from about 0 to about −0.5 with the contaminant-containing algal oil.

4. The method of claim 1, wherein the treatment conditions include a temperature of from about 4 to about 20° C.

5. The method of claim 1, wherein the treatment conditions include a temperature of from about 4 to about 15° C.

6. The method of claim 1, wherein the step of combining comprises combining the sulfuric acid-aqueous solution with the contaminant-containing algal oil at the treatment conditions that include a residence time of from about 30 minutes to about 8 hours, wherein the residence time is defined by an amount of time that the contaminant-containing algal oil is in contact with the sulfuric acid-aqueous solution to form the effluent.

7. The method of claim 1, wherein the step of combining comprises combining the sulfuric acid-aqueous solution with the contaminant-containing algal oil at the predetermined acid to oil ratio of from about 1:2 to about 2:1.

8. The method of claim 1, wherein the step of combining comprises combining the contaminant-containing algal oil with the sulfuric acid-aqueous solution that comprises sulfuric acid present in an amount of from about 1 to about 50 wt. % of the sulfuric acid-aqueous solution.

9. The method of claim 1, wherein the step of removing comprises separating the acidic aqueous phase from the effluent to form an acidic contaminant-containing aqueous solution, and the method further comprises the step of:

introducing a base-containing composition to the acidic contaminant-containing aqueous solution to neutralize the acidic contaminant-containing aqueous solution.

10. The method of claim 1, wherein the step of combining comprises combining the sulfuric acid-aqueous solution with the contaminant-containing algal oil that contains the contaminants comprising Ca, Fe, Mg, Na, Zn, K, P, or combinations thereof.

11. A method for removing contaminants from algal oil, the method comprising the steps of:

extracting a contaminant-containing algal oil from algae cells to form a crude algal oil that comprises the contaminant-containing algal oil and that is substantially free of the algae cells;

introducing the crude algal oil and a sulfuric acid-aqueous solution that has a pH of about 1 or less at a predetermined acid to oil ratio of from about 1:4 to about 4:1 to a reactor that is operating to a reactor that is operating at treatment conditions that include a temperature of from about 4 to about 25° C. to form an effluent that comprises a treated algal oil phase and contaminants in an acidic aqueous phase, wherein the contaminants comprise metals, phosphorus, or combinations thereof; and introducing the effluent to an oil-water separation zone to remove the acidic aqueous phase from the effluent and form a contaminant-depleted algal oil.

12. The method of claim 11, wherein the step of introducing the contaminant-containing algal oil comprises introducing the sulfuric acid-aqueous solution that has the pH of from about 1 to about −1 to the reactor.

13. The method of claim 11, wherein the step of introducing the contaminant-containing algal oil comprises operating the reactor at the treatment conditions that include a residence time of from about 30 minutes to about 8 hours, wherein the residence time is defined by an amount of time that the contaminant-containing algal oil is in contact with the sulfuric acid-aqueous solution to form the effluent.

14. The method of claim 11, wherein the step of introducing the effluent comprises separating the acidic aqueous phase from the effluent to form an acidic contaminant-containing aqueous solution, and the method further comprises the step of:

introducing the acidic contaminant-containing aqueous solution and a base-containing composition to a neutralizing zone to neutralize the acidic contaminant-containing aqueous solution with the base-containing composition.

15. The method of claim 11, wherein the treatment conditions include a temperature of from about 4 to about 20° C.

16. The method of claim 11, wherein the treatment conditions include a temperature of from about 4 to about 15° C.

17. A method for removing contaminants from algal oil, the method comprising the steps of:

extracting a contaminant-containing algal oil from algae cells to form a crude algal oil that comprises the contaminant-containing algal oil and that is substantially free of the algae cells;

introducing the crude algal oil and a sulfuric acid-aqueous solution at a predetermined acid to oil ratio of from about 1:4 to about 4:1 to a reactor that is operating at treatment conditions effective to form an effluent that comprises a treated algal oil phase and contaminants in an acidic aqueous phase including a temperature in the range of from about 4 to about 25° C., wherein the contaminants comprise metals, phosphorus, or combinations thereof and the sulfuric acid-aqueous solution comprises sulfuric acid that is present in an amount of from about 1 to about 50 wt. % of the sulfuric acid-aqueous solution, and wherein the predetermined acid to oil ratio is defined by a first weight of the sulfuric acid-aqueous solution to a second weight of the contaminant-containing algal oil; and introducing the effluent to an oil-water separation zone to remove the acidic aqueous phase from the effluent and form a contaminant-depleted algal oil.

18. The method of claim 17 wherein the temperature is in the range of from about 4 to about 20° C.

* * * * *